THORNLESS HONEY LOCUST TREE
Filed April 20, 1966 2 Sheets-Sheet 1
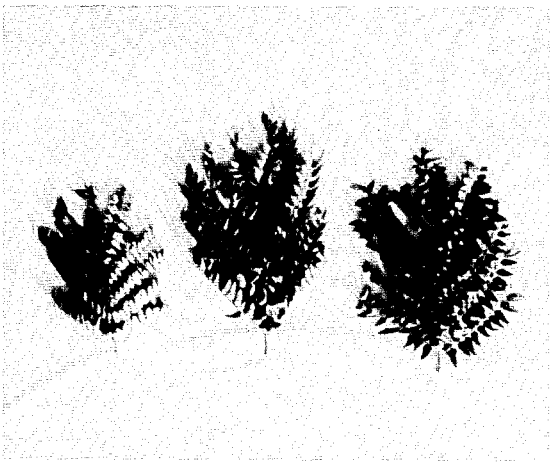
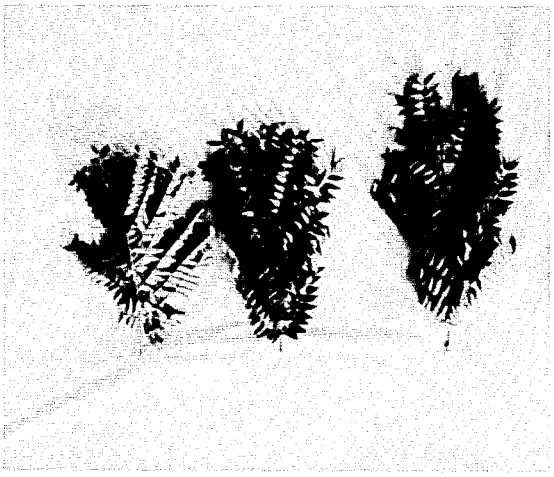

THORNLESS HONEY LOCUST TREE
Filed April 20, 1966 2 Sheets-Sheet 2
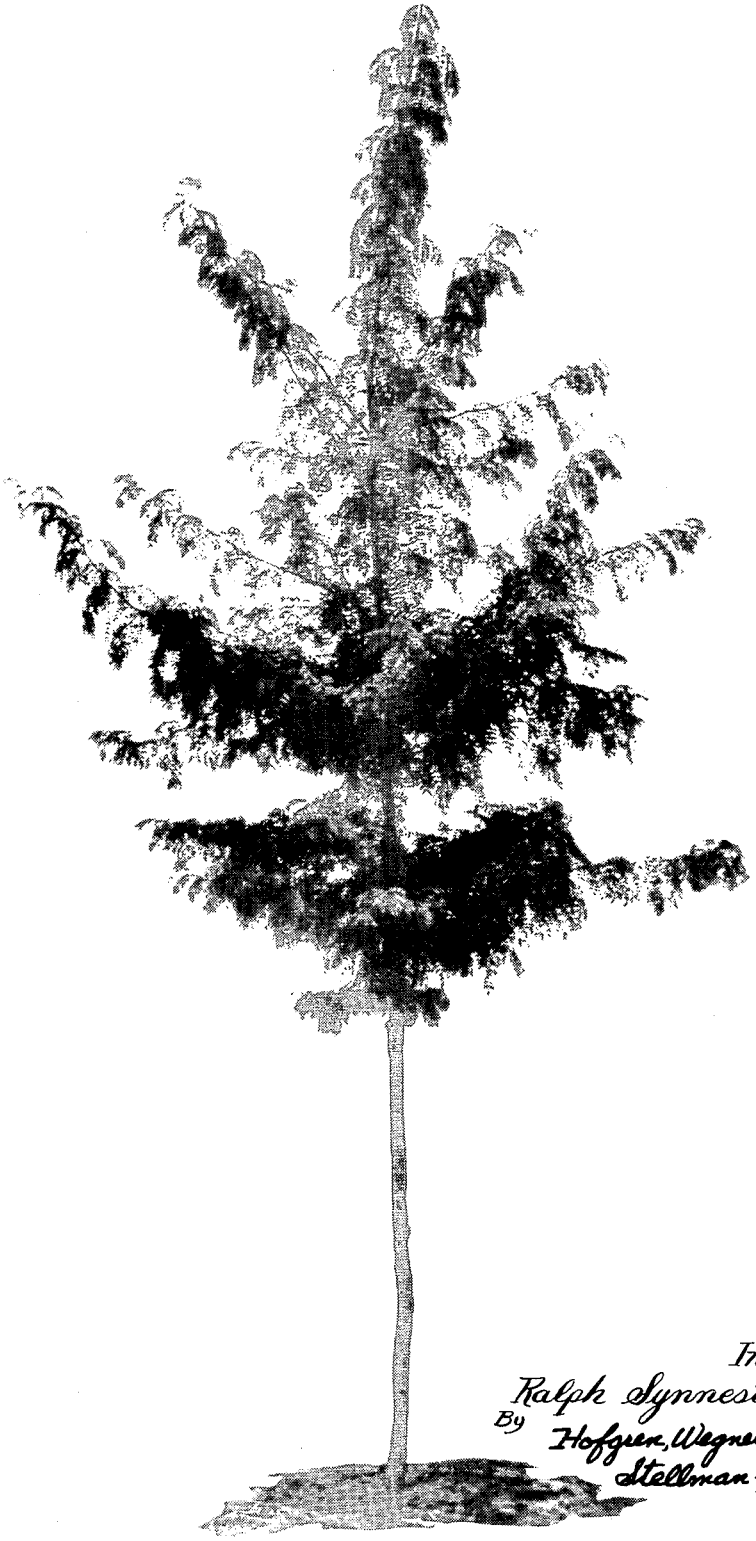
Inventor:
Ralph Synnestvedt
By Hofgren, Wegner, Allen, Stellman & McCord
Atty's United States Patent Office Plant Pat. 2,786
Patented Jan. 9, 1968

2,786
THORNLESS HONEY LOCUST TREE

Ralph Synnestvedt, Glenview, Ill., assignor of one-half to Carl G. Klehm, Arlington Heights, Ill.

Substituted for abandoned plant application Ser. No. 277,055, Apr. 30, 1963. This application Apr. 20, 1966, Ser. No. 551,477
1 Claim. (Cl. Plt.—52)

My invention relates to a new and distinct cultivar of thornless honey locust, or *Gleditsia triacanthos inermis*. The new cultivar, now over ten years old, is characterized by its symmetrical, broad, pyramidal habit of growth; dark green leaves; and its retention of the green foliage later than other known cultivars. Leaves were observed on my discovery, in Glenview, Ill., later in the fall than on other cultivars and up to two weeks later relative to Shademaster.

My new thornless honey locust tree has an extremely straight and unusually sturdy central leader; grows rapidly up to as high as an eight-foot branch tree in the first year from a bud; and retains its foliage much later in the season.

This honey locust tree was originated by me as a seedling from a block of over 12,000 seedlings grown, under my control, in my nursery in Glenview, Ill. This honey locust tree was asexually reproduced by me in Glenview, Ill. by budding and in Decherd, Tenn.

The accompanying illustrations show an entire plant and in natural color typical specimens of the foliage from one and two-year trees, showing both upper and lower surfaces.

The following is a detailed description of my new cultivar with color identifications in accordance with the Horticultural Colour Chart, vols. I and II, published by the British Colour Council in collaboration with the Royal Horticultural Society, except where general color terms of dictionary significance are obvious:

Parentage: A newly found seedling of *Gleditsia triacanthos inermis*, of unknown parentage.

Propagation: Holds it distinguishing characteristics through succeeding propagation by budding.

Locality where grown and observed: Glenview, Ill. and Decherd, Tenn.

Tree: Large; very vigorous upright, symmetrical with spreading branches, resulting in broad pyramidal head.

*Trunk.*—Smooth; straight central leader. Bark grayish-brown with slight gloss.

*Branches.*—Young branches slightly zig-zag; stout; color, Fern Green 0862/1, glossy; lenticals numerous, small light tan, slightly raised; 2 year branches, straight Willow Green 000862/1, masked with brown; lenticels larger, elliptical elongated, raised, reddish tan.

Foliage:

*Leaves.*—Medium to large; bipinnate, 10–18 pinnae per leaf and 16–28 leaflets per pinnae, holding later in the fall. Average length of leaves from 25–33 cm. Color: Upper surface, Spinach Green 0960; lower surface, Fern Green 0862/1.

*Leaflets.*—Ovate lanceolate, apex rounded; base, oblique. Average width of leaflet, 7–12 mm.; average length of leaflet, 17–30 mm. Margin, crenulate. Leaflets opposite near tip of rachis to alternate at the base.

*Rachis.*—Pubescent on the upper surface; slightly to inconspicuously grooved above.

*Petioles.*—Swollen at base, pubescent above.

*Stipules.*—Evident only on new leaves early in the spring; 1 cm. long.

Fruit: (Only one typical pod observed in ten years. Trees substantially seedless.)

Disease and insect resistance: The foliage is as resistant to common insect pest as compared with other cultivars grown under comparable cultural conditions.

My honey locust tree as a small tree maintains a central leader better than Shademaster and will self form a head without the pruning needed by other varieties.

My honey locust tree has a denser, heavier foliage than any other honey locust which tends to be heavier near the end of the new growth. The leaf area of the new growth of my tree is at least 15% to 20% heavier than Shademaster and at least 10% to 15% heavier than the Majestic tree.

My honey locust tree, as stated previously, holds leaves later in the fall, with this later leaf retention varying with the weather from year to year, but under observation being found to last from 10 to 17 days longer than the Shademaster tree and from 1 to 7 days longer than the Majestic tree.

My honey locust tree grows faster than other varieties under the same growing conditions, with several different observations supporting this. In the Glenview, Ill. nursery, after a growth period of several years, and with the trees growing side-by-side, my trees measured 5″–6″ in diameter, while Shademaster measured 4½″–5½″ and Majestic measured 4″–5″. In a Round Lake, Ill. nursery, 100 of my trees measured 3″, 3½″ and 4″ in diameter, while 100 Shademaster trees reached 2½″, 3″ and 3½″ in diameter. In one instance, a group of my trees grew to a diameter of 4″ in five years.

I claim:

1. A new and distinct cultivar of thornless honey locust tree with combination of features herein shown and described, characterized particularly by maintaining a central leader better as a small tree, growing much faster than other cultivars, having a denser and heavier foliage particularly near the end of the new growth, and retaining leaves much later in the fall as compared with other cultivars.

References Cited

UNITED STATES PATENTS

P.P. 1515 9/1956 Flemer ---------- P—52
P.P. 1534 12/1956 Cole ---------- P—52

ROBERT E. BAGWILL, *Primary Examiner.*